United States Patent [19]

Nalowaniec et al.

[11] Patent Number: 5,062,838

[45] Date of Patent: Nov. 5, 1991

[54] ABSORBENT DISPOSEABLE ARTICLE

[75] Inventors: Krzysztof Nalowaniec; Kurt Simmler, both of Heidenheim, Fed. Rep. of Germany

[73] Assignee: Paul Hartmann Aktiengesellschaft, Heidenheim, Fed. Rep. of Germany

[21] Appl. No.: 38,546

[22] Filed: Apr. 15, 1987

[30] Foreign Application Priority Data

Apr. 17, 1986 [DE] Fed. Rep. of Germany ....... 3613042

[51] Int. Cl.⁵ .............................................. A61F 13/15
[52] U.S. Cl. ................................... 604/366; 604/370; 604/378
[58] Field of Search ......................... 604/370, 365-367, 604/374, 375, 379, 381, 378

[56] References Cited

U.S. PATENT DOCUMENTS 3,604,422  9/1971  Sabee ................................... 604/365
3,779,246  12/1973  Mejek et al. ..................... 604/366 X
3,799,167  3/1974  Miller et al. ..................... 604/372 X
3,945,386  3/1976  Anczurowski et al. .
4,107,426  8/1978  Gordon ........................... 604/381 X

FOREIGN PATENT DOCUMENTS 0059015  2/1982  European Pat. Off. .
1914179  3/1969  Fed. Rep. of Germany .

Primary Examiner—Stephen C. Pellegrino
Assistant Examiner—Michael Rafa
Attorney, Agent, or Firm—Dick and Harris

[57] ABSTRACT

An absorbent disposable article including an absorbent body covered, on one side by an impervious sheet, and on the other side, by a porous cover layer. An impermeable protective layer, having a coarse side and a smooth side, is provided along the edges of the porous cover layer, with the coarse side facing the porous cover layer. The impermeable protective layer is pressure bonded to the porous cover layer to produce a liquid impervious barrier.

8 Claims, 3 Drawing Sheets

ABSORBENT DISPOSEABLE ARTICLE

BACKGROUND OF THE INVENTION

The invention concerns an absorbent disposable article, such as in particular a diaper including, in part, an absorbent body having a liquid-permeable protective sheet on one side and a porous cover layer on an opposite side.

Such articles are known, for example, from German Published Patent Application 19 14 179 and European Patent 00 59 015 81.

In both cases, individual sheets are laid up as barrier layers, which either are bonded only on the edge of the disposable article to the porous cover layer (GPPA. 19 14 179) or, for edge reinforcement, are also additionally bonded to the cover layer at further locations disposed, respectively, at a distance from one another, distributed over the entire surface of the barrier layer (EP 0 059 015 B1).

The drawback of these barrier layers consists in that they represent in principle in each case an independent layer, which is bonded to the cover layer solely in individual spots. Because of that, these barrier layers must exhibit, i.a., a thickness which imparts to them an independently sufficient strength. Therefore, these barrier layers require a relatively large amount of material. In the case of the class of mass-produced articles, this already is of consequence from the standpoint of cost. Also, those layers are unpleasantly stiff in wear.

It is, moreover, already known from U.S. Pat. No. 3,799,167 to produce the corresponding barrier layers at the edge of an absorbent disposable article through impregnation of the porous cover layer with a liquid-impermeable material. The shortcoming of this embodiment consists in that again a relatively higher expenditure of material is required in order to achieve an assured imperviousness of the layer by complete filling of the pores of the cover layer. As a result of the complete penetration into the pores in the course of impregnation of the liquid-impermeable filler materials, the cover layer is quite hard and relatively stiff. In the cases where the disposable article to be produced comes with the cover layer in contact with the skin of the person wearing the disposable article on his or her body, this is perceived as unpleasant; then, in the case of disposable articles to be worn on the body, a porous cover layer directly adjacent the skin is made from a soft, pleasant to wear material. These pleasant to wear properties, naturally, are not possessed by a liquid-impermeable filler material.

In the case of a further absorbent disposable article, known from U.S. Pat. No. 3,604,422, a liquid-impermeable coating can, i.a., be applied to the porous cover layer. When, on the other hand, applying such a coating, as again according to U.S. Pat. No. 3,799,167, in most cases, an undesirably deep penetration by the liquid-impermeable material being applied occurs. Too deep a penetration of the material forming the barrier layer is undesirable also for reasons already enumerated in the above-cited U.S. Pat. No. 3,799,167.

SUMMARY OF THE INVENTION

Starting from the above-mentioned state of the art, the problem underlying the invention is to provide an absolutely impervious and mechanically sufficiently strong liquid-impermeable layer with any desired predetermined surface stretching, while employing the smallest possible amount of material. At the same time, it should be assured in this connection that the side of the cover layer turned toward the wearer is absolutely free from the material from which the particular liquid-impermeable layer is formed. Further, the softness of the cover layer should be impaired as little as possible by the liquid-impermeable layer.

This problem is solved by that the cover layer of the disposable absorbent article of this kind is provided with a liquid-impermeable layer which consists of a heat-sealable, especially thermoplastic, material, which in the form of a prefabricated impervious sheet, penetrates with physical bonding over its entire area in any desired predetermined regions into the surface of the porous cover layer only to a small degree, without altogether penetrating this cover layer even approximately completely.

The minimized expenditure of material strived for in the formation of the liquid barrier layer is for that purpose achieved by that the barrier layer is a prefabricated sheet of an adhesive material, which is brought onto the cover layer of the disposable article solely under a light pressure over the entire surface.

While the material, on the one hand should penetrate over its entire area into the surface of the cover layer only to a small degree, in order to obtain, together with the material of the cover layer, bonding of the materials of both layers required for a sufficient strength of the barrier layer; the voids lying under the surface of the cover layer should on the other hand be filled only to the extent absolutely required for achieving a strong bond, for reasons of the least possible employment of the layer material.

In order to obtain this in the best way, the impervious sheet exhibits in its prefabricated state two differently shaped surfaces. The surface of the impervious sheet not in contact with the cover layer, which lies on the absorbent body of the disposable article is formed as smooth as possible in order to assure absolute imperviousness of the sheet even at the smallest thicknesses. The surface adjacent the surface of the cover layer, to the contrary, is best of an extremely coarse structure since this assures a physically outstanding bond between the impervious sheet and the cover layer even when the material of the impervious sheet quantitatively penetrates into the cover layer altogether only to an exceedingly small degree.

It is particularly advantageous when the impervious sheet penetrates into the cover layer only to the depth of the coarse surface. It thus is possible that for a maximum penetration of the highest peaks of about 15 to 30 $\mu$m, the depth of the penetration, averaged over the entire surface of the sheet, lies at only about 5 $\mu$m.

In this manner, impervious sheets can be employed which, especially when they consist of a material based on copolymers of alpha-olefins, exhibit surface weights of only 20 to 30 g/m$^2$, especially even only 20 to 25 g/m$^2$.

An advantageous process for the manufacture of the articles of the invention consists in that the impervious sheet with one smooth and one coarse surface is produced so that the thermoplastic, liquid-impermeable layer-forming material is applied in the molten state onto the open smooth surface of a rotating, especially cooled, roll.

In order to assure that during the application of the impervious sheet to the cover layer occurring solely under transfer pressure the material of the impervious sheet does not penetrate into the cover layer throughout the entire depth of the sheet, the impervious sheet has during its application exclusively on its surface facing the cover layer plastic deformability within a range of the thickness that is smaller than the entire thickness of the impervious sheet. The differential plastic deformability of the impervious sheet throughout its thickness can be obtained during its application to the cover layer by that the temperature across the thickness of the sheet decreases in such a manner from the surface adjacent the cover layer that on the free, smooth surface of the sheet plastic deformability is no longer possible.

A process by which such a tempering of the impervious sheet during its application to the cover layer can be achieved in an exceedingly simple and economical manner consists in that a heat-sealable, especially a thermoplastic material is dispensed in a molten state onto the surface of a rotating roll whose temperature is lower than the temperature of the environment, and that the impervious sheet forming on the roll is brought directly from the roll with its surface not adjacent the roll upon the cover layer.

In the case of absorbent articles which are cut by the piece from continuous lengths of web material covering individual absorbent bodies spaced behind one another, and only in individual regions extending perpendicularly to the feed direction of the web material (e.g., waist closure areas of diapers) exhibit impervious sheets, which are respectively provided in a discontinuous manner, will the impervious sheet-producing heat-sealable, especially thermoplastic, material be dispensed in a molten state in a correspondingly discontinuous manner onto a rotating roll and from there as an individual impervious sheet member directly transferred onto the continuous running cover layer web material.

In the case of the liquid-impermeable layers of the invention, it is possible to reinforce in a very simple manner the physical bond between the impervious sheet and the cover layer in individual predetermined sections of the surface. Such reinforcements may be desired, e.g., in diapers in those areas to which the adhesive strips for closing the diapers on the body of the wearer are to be attached, or in the outermost edge areas of the diaper wherein the outer protective sheet is bonded to the cover layer. In the last-named case, the impervious sheet can even be employed as adhesive to achieve the desired bond. In order to obtain this or, respectively a noteworthy reinforcement of the cover layer material, the impervious sheet is made plastic in the corresponding locally limited region or, as the case may be, up to its entire depth, whereby the cover layer can be completely penetrated throughout during the application. By making the material of the impervious sheet penetrate completely throughout the cover layer, in all those places where the cover layer lies directly on the protective sheet, a common strong bond is obtainable. In this manner, e.g., the tear-off strength of the adhesive closing strips on the diapers can be considerably increased.

The zones of differential plastic deformability of the impervious sheet can be quite advantageously obtained during the production of the impervious sheet on a rotating roll and its immediate subsequent transfer onto the article being manufactured by that the regions of complete plastic deformability of the impervious sheet are produced by decreased cooling of the corresponding areas of the roll.

Irrespective of the complete penetration of the material of the impervious sheet into the regions to be reinforced of the article according to the invention, those regions can also be additionally reinforced by that local thickenings of the impervious sheet can be provided. The thickenings of the impervious sheet can be predetermined, e.g., through the application of the starting material for the impervious sheet in different thickness onto the impervious sheet-producing rotating roll.

BRIEF DESCRIPTION OF THE DRAWINGS

FIG. 6 is a partial cross section of an alternative preferred embodiment of the invention with an impervious sheet that is thickened in the region of attachment of the adhesive closure strips; and FIG. 7 is a partial cross section of an alternative preferred embodiment of the invention, showing an impervious sheet which is thickened and is substantially completely pressed into the porous cover sheet.

DETAILED DESCRIPTION OF THE DRAWINGS

Figure 1:
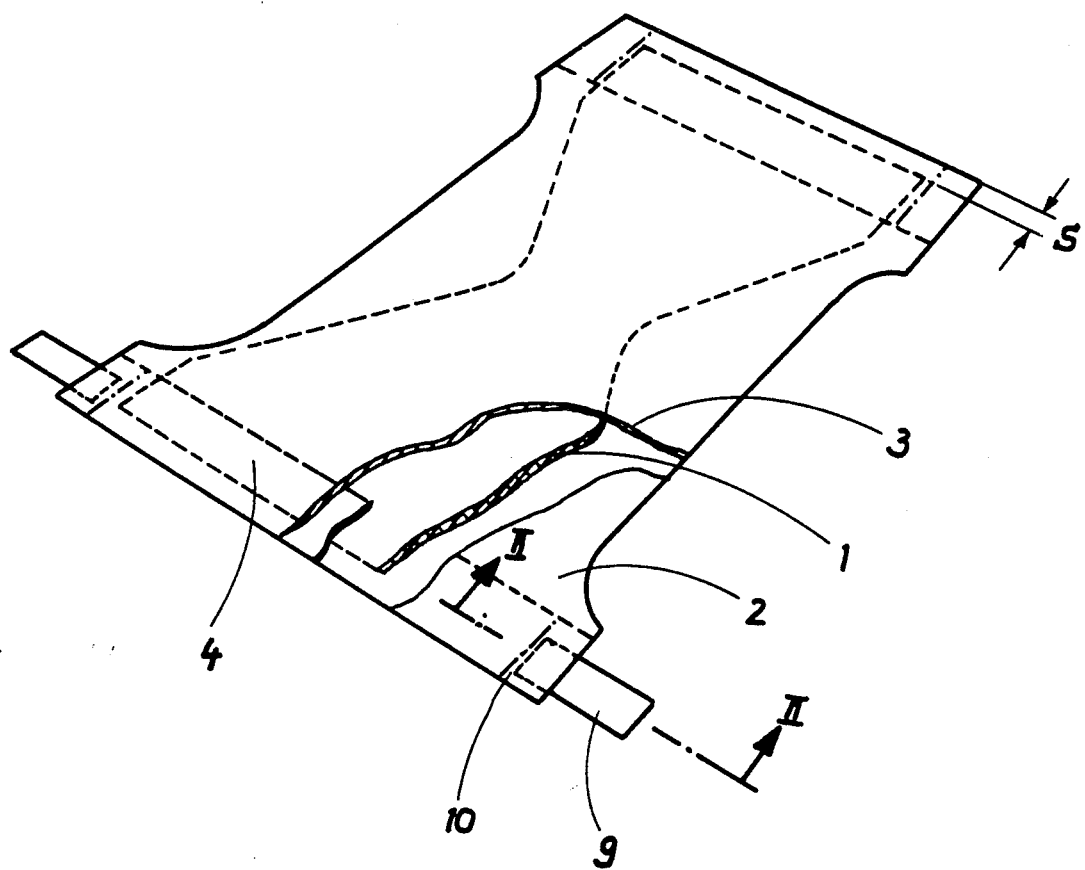
FIG. 1 is a diaper perspective view with open edge area.

While this invention is susceptible of embodiment in many different forms, there is shown in the drawings and will be herein described in detail, a specific embodiment with the understanding that the present disclosure is to be considered as an exemplification of the principles of the invention and is not intended to limit the invention to the embodiment illustrated. A diaper consists of an absorbent material 1 which is covered on one side with a liquid-impermeable protective sheet 2 and on the other side with a fleece as porous cover layer 3. The protective sheet 2 and the cover layer 3 are glued to each other on the edges of the diaper.

In order to prevent seepage in the waist area of the diaper through the cover layer 3 of the liquid present in the porous body, there is provided in each case an impervious sheet 4 running as a strip-shaped liquid-barrier layer.

This impervious sheet 4 consists of the thermoplastic alpha-olefin copolymer material. It is applied to the cover layer 3 in a prefabricated form.

The manufacture and subsequent bringing of the impervious sheet 4 onto the cover layer 3 take place in the following manner:

The thermoplastic material forming the impervious sheet 4 is dispensed intermittently in a molten state onto a rotating cooled roll 5 with a smooth surface from a spray nozzle 6.

Figure 5:
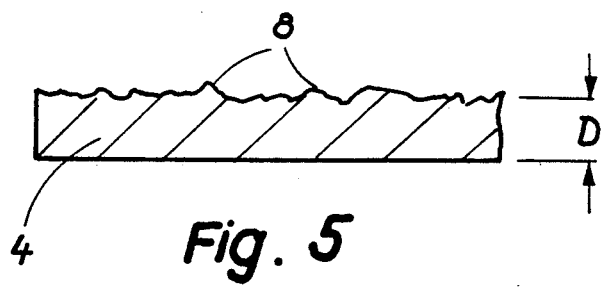
FIG. 5 is a partial cross-section through an impervious sheet along the line V—V.

The average thickness of the formed highly coarse surface of the impervious sheet facing away from the surface of the roll amounts to $D = 22$ μm (the average thickness is represented in FIG. 5). The surface weight of the impervious sheet 4 amounts to 25 g/m². Cooling of the roll 5 is so adjusted that essentially only the material lying in the coarse surface of the impervious sheet 4 still has plastic deformability while this, especially on the surface of the impervious sheet adjacent the surface of the roll, certainly no longer is the case. In this state, the individual sections of the impervious sheet 4 are transferred under only a light pressure onto the cover layer 3 fed as continuous web goods 7. The continuous web material 7 thus bonded with the impervious sheet 4 is thereafter brought upon the protective sheet 2 likewise fed as a continuous web goods, already containing the porous body 1 spaced from one another, whereby the cover layer 3 and the protective sheet 2 are bonded with each other on the edges of the diaper. The impervious sheet sections 4 which are placed at the waist-closing edges of the diaper can be employed as the adhesive material in the regions S extending in the perpendicular direction between the porous bodies 1 (FIG. 1). Bonding can proceed so that in those regions the superimposed layers are subjected to local heat sealing.

The impervious sheet 4 brought under only a light pressure onto the cover layer 3 penetrates only with the material peaks 8 into the cover layer 3. On these material peaks the physical bonding strived for is attained, which is necessary in order to assure a stable position of extremely thin sheets in the diapers. On the other hand, there always remains during the process of laying up a region of the impervious sheet that does not have plastic deformability, which is aligned on the cover layer 3 with a securely closed surface and provides for the required imperviousness.

Figure 3:
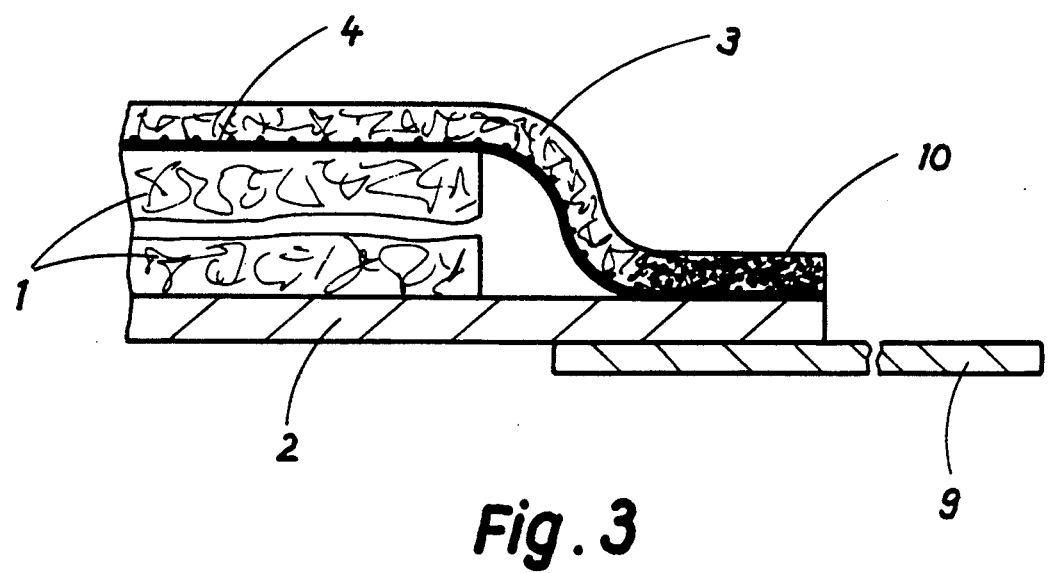
FIG. 3 is a partial cross-section of FIG. 2 with a modified attachment of the impervious sheet in the edge area of the cover layer.

In the case when a region of the diaper within which adhesive closing strips 9 are to be attached to the impervious sheet 2 should be additionally reinforced, the impervious sheet material 4 can there be completely pressed into the cover layer material 3. This is shown in FIG. 3, wherein the impervious sheet material 4 practically completely penetrates through the cover layer material 3 in the corresponding edge area 10. These edge areas 10 lying under the adhesive closing strips 9 are shown in FIG. 1 with dot and dash lines.

Figure 2:
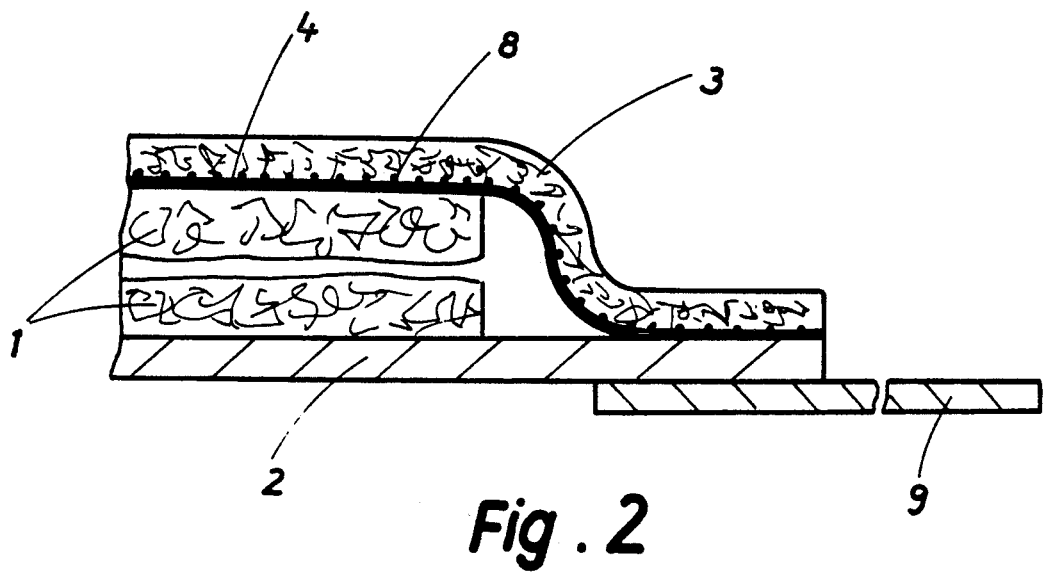
FIG. 2 is a partial cross-section along the line II—II.
Figure 4:
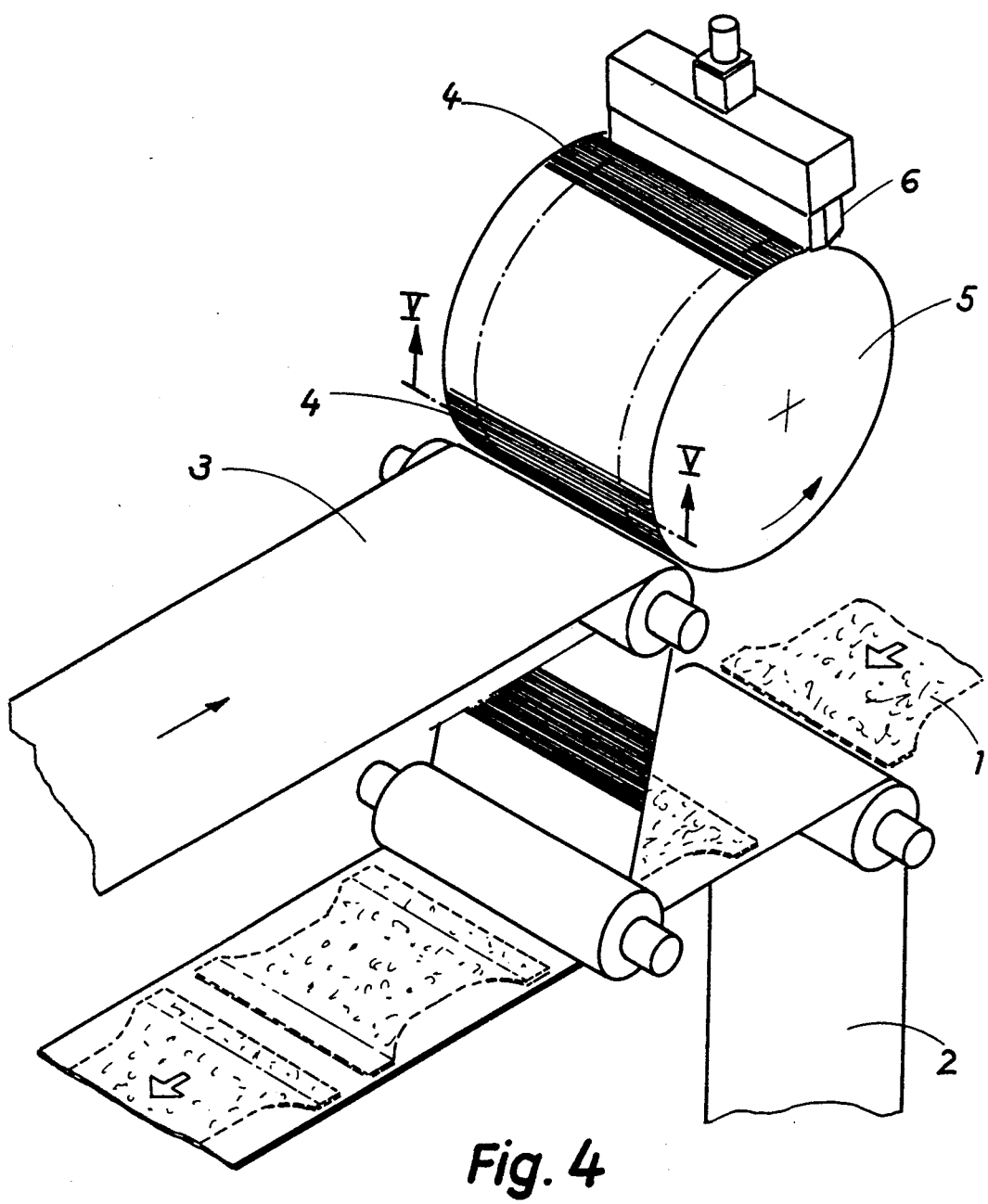
FIG. 4 is a perspective view of a manufacturing device for the manufacture of an impervious sheet and its bringing upon a continuously fed continuous web material.

Likewise, in FIG. 4 dot and dash lines are shown on the roll 5, which there indicate those regions in the corresponding manner. The edge area extending on the roll 5 from each dot and dash line to the edge of the roll is cooled to a lesser degree when the impervious sheet should completely penetrate into the cover layer material. As previously indicated, an alternative method of reinforcement, in the areas of the adhesive closing strips, involves providing for a thickening of the impervious sheet in the regions of attachment of the adhesive closing strips. FIG. 6 shows a configuration similar to that of FIG. 2, but impervious layer 4 includes a thickened region 11 in the area of the adhesive closing strip 9. Alternatively, the thickened area 11 may also be utilized with the technique of completely pressing impervious sheet material 4 into cover layer 3, as illustrated in FIG. 7. Because of this, the impervious sheet retains plastic deformability during the application to the cover layer over its entire depth in those regions.

If the impervious sheet is not brought directly after its formation on a rotating roll in the same process step onto the cover layer 3, it must be reheated, and indeed so that the above-described differential plastic deformability or, respectively, local nondeformability is obtained.

We claim:

1. An absorbent disposable article for absorbing and retaining moisture, such as, for example, a diaper, and of the type including an absorbent body means having first and second sides and a boundary edge region, liquid impermeable protective sheet means operably arranged along said first side of said absorbent body means, porous cover layer means operably arranged along said second side of said absorbent body means, and further of the type wherein said liquid impermeable protective sheet means and said porous cover layer means extend beyond at least a portion of said boundary edge region of said absorbent body means and are there bonded together, said absorbent disposable article comprising:

a liquid barrier layer means being arranged along at least a portion of said boundary edge region, interposed between said porous cover layer means and said absorbent body means and likewise interposed between said porous cover layer means and said liquid impermeable protective sheet means, said liquid barrier layer means being continuously physically bonded to and extending into said porous cover layer means without penetrating completely through said porous cover layer means, said liquid barrier layer means being fabricated of a heat sealable thermoplastic material in the form of a prefabricated impervious sheet.

2. The invention according to claim 1 wherein said liquid barrier layer means extends into said porous cover layer means to a maximum depth of 7 micrometers.

3. The invention according to claim 1 wherein said liquid barrier layer means includes a coarse surface and an oppositely arranged substantially smooth surface.

4. The invention according to claim 3 wherein said coarse surface of said liquid barrier layer means in juxtaposed with and, upon said physical bonding, extends into said porous cover layer means.

5. The invention according to claim 4, wherein said coarse surface of said liquid barrier layer means extends into said porous cover layer means to an average depth of 5 micrometers.

6. The invention according to claim 1, wherein said porous cover layer means comprises a sheet fabricated of an alpha-olefin copolymer material having a mass per unit area of from 20 to 30 grams per square meter.

7. The invention according to claim 1 further comprising:

adhesive closure strip means operably affixed to said liquid impermeable protective sheet means, for facilitated removable securement of said absorbent disposable article to a wearer's body, said liquid barrier layer means, being approximately completely embedded within said porous cover layer means, proximate to said region of affixation of said adhesive closure strip means to said liquid impermeable sheet means toward providing increased resistance to localized stresses and tearing.

8. The invention according to claim 7 wherein said liquid barrier means has a variable thickness, which thickness is increased proximate to said region of affixation of said adhesive closure strip means to said liquid impermeable protective sheet means.

* * * * *

UNITED STATES PATENT AND TRADEMARK OFFICE
CERTIFICATE OF CORRECTION

PATENT NO. : 5,062,838

DATED : November 5, 1991

INVENTOR(S) : Malowaniec, et al.

It is certified that error appears in the above-identified patent and that said Letters Patent is hereby corrected as shown below:

On the title page:

Item [19] Should read --Malowaniec et al.--.

Item [75] Should read --Krzysztof Malowaniec, Kurt Simmler, both of Heidenheim, Fed. Rep. of Germany--.

Col. 4, Line 10   Delete "thickness" and instead insert --thicknesses--.

Signed and Sealed this

Thirtieth Day of March, 1993

Attest:

STEPHEN G. KUNIN

*Attesting Officer*   Acting Commissioner of Patents and Trademarks